US005792832A

United States Patent [19]
Lange, III et al.

[11] Patent Number: 5,792,832
[45] Date of Patent: Aug. 11, 1998

[54] PEPTIDES FROM MAMMALIAN PANCREATIC CHOLESTEROL ESTERASE

[76] Inventors: Louis George Lange, III, 38 Kingsbury Pl., St. Louis, Mo. 63112; Curtis A. Spilburg, 2230 Willow Ridge La., Chesterfield, Mo. 63017

[21] Appl. No.: 461,881

[22] Filed: Jun. 5, 1995

Related U.S. Application Data

[62] Division of Ser. No. 350,801, Dec. 7, 1994, abandoned, which is a continuation of Ser. No. 856,910, May 12, 1992, abandoned, which is a continuation of Ser. No. 439,899, Nov. 20, 1989, Pat. No. 5,100,510.

[51] Int. Cl.$^6$ .............................. C07K 7/06; C07K 9/00; C12N 9/16
[52] U.S. Cl. .............. 530/329; 530/328; 530/350; 435/196
[58] Field of Search .............. 530/329, 328, 530/327, 326, 325, 324, 350; 435/196

[56] References Cited

U.S. PATENT DOCUMENTS

| | | |
|---|---|---|
| 4,732,757 | 3/1988 | Stolle et al. .............. 424/87 |
| 4,944,944 | 7/1990 | Tang et al. .............. 424/94.6 |
| 5,017,565 | 5/1991 | Lange, III et al. .............. 514/54 |
| 5,063,210 | 11/1991 | Lange, III et al. .............. 514/54 |
| 5,173,408 | 12/1992 | Lange, III et al. .............. 435/69.1 |
| 5,200,183 | 4/1993 | Tang et al. .............. 424/94.6 |
| 5,210,183 | 5/1993 | Lindahl et al. .............. 530/350 |
| 5,352,601 | 10/1994 | Lange, III et al. .............. 435/196 |
| 5,432,058 | 7/1995 | Lange, III et al. .............. 435/11 |

FOREIGN PATENT DOCUMENTS 9012579 11/1993 European Pat. Off. ..... A61K 31/725

OTHER PUBLICATIONS

Kyger et al., Biochemical and Biophysical Research Communications, 164(3); 1302–1309 (1989).
Custer et al., Am. J. Physiol., 266: F767–F774 (1994).
Bosner et al., Proc. Natl. Acad. Sci. USA, 85: 7438–7442 (1988).
Vahouny et al., Proc. J. Exp. Biol. Med., 116: 496 (1964).
Casdorph, Richard H., Cholestyramine and Ion–Exchange Resins, pp. 221–256 (date N.A.).
Wagner, Richard W., Nature, 372: 333–335 (1994).
Ullrich et al., The EMBO Journal, 3(2): 3621–4 (1984).
Werner et al., J. Biol. Chem., 269: 6637–6639 (1994).
Abouakil et al., Biochemica et Biophysica Acta, 961: 299–308 (1988).
Han et al., Biochemsitry, 26: 1617–25 (1987).
Neckers et al., Am. J. Phyusiol, 265: L1–L12 (1993).
Stoll et al., Biochem. J., 180: 465–470 (1979).
Labow et al., Arch Biochem. Biophys. Acta, 749: 32–41 (1975).
Brown et al., Biochem. Biophys. Acta, 769: 471–478 (1984).
Rudd et al., Biochemica et Biophysica Acta, 918: 106–114 (1987).
Jaye et al., Nucleic Acids Research, 11(8): 2325–2335 (1983).
Cossum et al., J. Pharmacol. Exper. Therapeutics, 267: 1181–1190 (1993).
Fitzpatrick et al., Journal of Virology, 62: 4239–4248 (1988).
Cohen, Jack S., Advances in Pharmacology, 25: 319–339 (1994).
Tenehouse et al., J. Clin. Invest., 93:671–676 (1994).
Gao et al., Molec. Pharacol., 43: 45–50 (1993).
Emtage et al., Proc. Natl. Acad. Sci. USA, 80: 3671–75 (1983).
Dean et al., Proc. Natl. Acad. Sci. USA, 91: 11762–11766 (1994).
Leonetti et al., Proc. Natl. Acad. Sci. USA, 88: 2702–2706 (1991).
Yakubov et al., Proc. Natl. Acad. Sci. USA, 86:6454–6458 (1989).
Zamecnik et al., Proc. Natl. Acad. Sci. USA, 91: 3156–3160 (1994).
Magagnin et al., Proc. Natl. Acad. Sci. USA, 90: 5979–5983 (1993).
Agrawal et al., Proc. Natl. Acad. Sci. USA, 88: 7595–7599 (1991).
Morishita et al., Proc. Natl. Acad. Sci. USA, 90: 8474–8478 (1993).
Ratajczak et al., Proc. Natl. Acad. Sci. USA, 89: 11823–11827 (1992).
Towbin et al., Proc. Natl. Acad. Sci. USA, 76: 4350–4354 (1979).
Stein et al., Science, 261: 1004–1012 (1993).
Laemmli, U.K., Nature, 227: 680–685 (1970).
Simons et al., Nature, 359: 67–70 (1992).
Allain et al., Clin. Chem., 20: 470 (1974).

*Primary Examiner*—Keith D. Hendricks
*Attorney, Agent, or Firm*—McDonnell Boehnen Hulbert & Berghoff

[57] ABSTRACT

The invention provides methods for the purification to homogeneity of pancreatic cholesterol esterase in useful quantities from a variety of mammalian species. The gene for a mammalian pancreatic cholesterol esterase has been cloned and sequenced, and is useful for expressing cholesterol esterase in a transformed eukaryotic or prokaryotic cell culture. Thus, methods according to the invention enable the production of large quantities of pancreatic cholesterol esterase for the screening of inhibitors, the production of antibodies, and for commercial purposes related to the alteration of cholesterol/cholesterol ester composition of materials containing free or esterified cholesterol.

2 Claims, 7 Drawing Sheets

FIG. 1

```
         10         20         30         40         50
LGASRLGPSP GCLAVASAAK LGSVYTEGGF VEGVNKKLSL FGDSVDIFKG
         60         70         80         90        100
IPFAAAPKAL EKPERHPGWQ GTLKAKSFKK RCLQATLTQD STYGNEDCLY
        110        120        130        140        150
LNIWVPQGRK EVSHDLPVMI WIYGGAFLMG ASQGANFLSN YLYDGEEIAT
        160        170        180        190        200
RGNVIVVTFN YRVGPLGFLS TGDSNLPGNY GLWDQHMAIA WVKRNIEAFG
        210        220        230        240        250
GDPDNITLFG ESAGGASVSL QTLSPYNKGL IKRAISQSCV GLCPWAIQQD
        260        270        280        290        300
PLFWAKRIAE KVGCPVDDTS KMAGCLKITD PRALTLAYKL PLGSTEYPKL
        310        320        330        340        350
HYLSFVPVID GDFIPDDPVN LYANAADVDY IAGTNDMDGH LFVGMDVPAI
        360        370        380        390        400
NSNKQDVTEE DFYKLVSGLT VTKGLRGANA TYEVYTEPWA QDSSQETRKK
        410        420        430        440        450
TMVDLETDIL FLIPTKIAVA QHKSHAKSAN TYTYLFSQPS RMPIYPKWMG
        460        470        480        490        500
ADHADDLQYV FGKPFATPLG YRAQDRTVSK AMIAYWTNFA RTGDPNTGHS
        510        520        530        540        550
YVPANWDPYT LEDDNYLEIN KQMDSNSMKL HLRTNYLQFW TQTYQALPTV
        560        570        580        590
TSAGASLLPP EDNSQASPVP PADNSGAPTE PSAGDSEVAQ MPVVIGF
```

FIG. 2a

```
                                      10         20
                             GCCTAGAGGC AGACACTCAC TATGGGGCG
      10         20         30         40         50
      *          *          *          *          *
GCTGGGAGCT AGCCGTCTTG GGCCGTCGCC TGGCTGCTTG GCAGTAGCGA
30        40         50        60         70
cCTGGAgGtT CTGTTTCT-T GGC-cTCACC -TGCTGCTTG GCAGcTGCTT
      60         70         80         90        100
      *          *          *          *          *
GTGCAGCGAA GTTGGGCTCC GTATACACCG AAGGCGGCTT CGTGGAGGGC
       80        90       100        110       120
GTGCTGCAAA GTTGGGTGCT CTGTACACAG AAGGCGGTTT TGTGGAGGGC
     110        120        130        140        150
      *          *          *          *          *
GTCAACAAGA AGCTGAGCCT CTTTGGCGAC TCTGTTGACA TCTTCAAGGG
                                 TGG
      130        140        :         160        170        180
GTCAACAAGA AACTcAGTCT CTGTGGTGAC TCTGTTGACA TCTTCAAGGG
     160        170        180        190        200
      *          *          *          *          *
CATCCCCTTC GCTGCCGCCC CCAAGGCCCT GGAGAAGCCC GAGCGACACC
            190        200        210        220
CATCCCCTTC GCTACC---G CCAAGACCCT GGAGAATCCT cAGCGTCACC
     210        220        230        240        250
      *          *          *          *          *
CCGGCTGGCA AGGGACCCTG AAGGCCAAGA GCTTTAAGAA ACGGTGCCTG
                                 A
      230        240        250  .      260        270
CTGGCTGGCA AGGACACTG AAGGCTCAG- ACTTCAAGAA ACGATGTCTA
     260        270        280        290        300
      *          *          *          *          *
CAGGCCACGC TCACGCAGGA CAGCACCTAC GGAAATGAAG ACTGCCTCTA
      280        290        300        310        320
CAAGCCACCa TCACCCAGGA TGATACCTAT GGgCAAGAAG ACTGCCTCTA
     310        320        330        340        350
      *          *          *          *          *
CCTCAACATC TGGGTCCCCC AGGGCAGGAA GGAAGTCTCC CACGACCTGC
      330        340        350        360        370
TCTCAACATC TGGGTCCCTC AGGGCAGGAA GcAAGTGTCT CATGACCTGC
```

FIG. 2b

```
         *  360       *  370       *  380       *  390       *  400
       CCGTCATGAT  CTGGATCTAT  GGAGGCGCCT  TCCTCATGGG  GGCCAGCCAA
          380         390         400         410         420
       CTGTgATGgT  CTGGATCTAT  GGAGGtGCCT  TCCTCATGGG  GtCTGGCCAg

*  410       *  420       *  430       *  440       *  450
       GGGGCCAACT  TTCTCAGCAA  CTACCTCTAC  GACGGGGAGG  AGATTGCCAC
          430         440         450         460         470
       GGaGCCAAtT  TTCTCAaGAA  tTACCTgTAt  GATGGGGAaG  AGATcGCCAC

*  460       *  470       *  480       *  490       *  500
       ACGGGGCAAC  GTCATCGTGG  TCACGTTCAA  CTACCGCGTT  GGGCCCCTGG
          480         490         500         510         520
       tAGAGcCAAt  GTCATtGTGG  TCACcTTCAA  CTACCGtGTc  GGaCCCtTGG

*  510       *  520       *  530       *  540       *  550
       GCTTTCTCAG  CACCGGGGAC  TCCAACCTGC  CAGGTAACTA  TGGCCTTTGG
          530         540         550         560         570
       GtTTcCTtAG  CACCGGaGAt  gCTAACCTtC  CAGGTAACTt  TGGACTTcGA

*  560       *  570       *  580       *  590       *  600
       GATCAGCACA  TGGCCATTGC  TTGGGTGAAG  AGGAACATTG  AGGCCTTCGG
          580         590         600         610         620
       GATCAGCACA  TGGCtATTGC  cTGGGTGAAG  AGGAACATTG  CAgCCTTtGG

*  610       *  620       *  630       *  640       *  650
       AGGAGACCCC  GACAACATCA  CCCTCTTTGG  GGAGTCGGCC  GGAGGCGCCA
          630         640         650         660         670
       AGGAGACCCC  GAtAACATCA  CCaTCTTTGG  GGAATCTGCT  GGAGGTGCCA

*  660       *  670       *  680       *  690       *  700
       GCGTCTCTCT  GCAGACCCTC  TCTCCCTACA  ACAAGGGCCT  CATCAAGCGA
```

FIG. 2c

```
     680        690        700        710        720
TTGTCTCTCT GCAGACCCTC TCcCCaTACA ACAAGGGCCT CATCcGGCGA
   * 710      * 720      * 730      * 740      * 750
GCCATCAGCC AGAGTGGAGT GGGTTTGTGC CCTTGGGCCA TCCAGCAGGA
     730        740        750        760        770
GCCATCAGTc AGAGTGGTGT GGcacTGAGC CCcTGGGCCA TCCAGgAGAA
   * 760      * 770      * 780      * 790      * 800
CCCCCTCTTC TGGGCTAAAA GGATTGCAGA GAAGGTGGGC TGCCCCGTGG
     780        790        800        810        820
TCCACTTTTC TGGGCcAAAA cGATcGCTAA GAAGGTGGGa TGCCCCAcAG
   * 810      * 820      * 830      * 840      * 850
ACGACACCAG CAAGATGGCT GGGTGTCTGA AGATCACTGA.CCCCCGTGCC
     830        840        850        860        870
AtGAtACCgc CAAGATGGCT GGGTGTCTGA AGATCACaGA tCCCCGaGCC
   * 860      * 870      * 880      * 890      * 900
CTGACGCTGG CCTATAAGCT GCCCCTGGGA AGCACGGAAT ACCCCAAGCT
     880        890        900        910        920
tTGACaCTGG CCTAcAgGtT GCCCtTGAaA AGCcAGGAGt ACCCCAttGT
   * 910      * 920      * 930      * 940      * 950
GCACTATCTG TCCTTCGTCC CCGTCATCGA TGGAGACTTC ATCCCTGATG
     930        940        950        960        970
GCACTAcCTG gCCTTCATCC CTGTCgTCGA TGGTGACTTC ATTCCTGATG
   * 960      * 970      * 980      * 990      * 1000
ACCCCGTCAA CCTGTACGCC AACGCCGCGG ACGTCGACTA CATAGCGGGC
     980        990       1000       1010       1020
AtCCCATCAA CCTGTACGAC AACGCtGCTG ACATTGACTA CTTAGCGGGT
```

FIG. 2d

```
       1010        1020        1030        1040        1050
        *           *           *           *           *
   ACCAATGACA  TGGACGGCCA  CCTCTTTGTC  GGGATGGACG  TGCCAGCCAT
   1030        1040        1050        1060        1070
   AtTAATGACA  TGGAtGGCCA  CCTgTTTGcT  AcAgTTGACG  TGCCcGCCAT 1060        1070        1080        1090        1100
        *           *           *           *           *
   CAACAGCAAC  AAACAGGACG  TCACGGAGGA  GGACTTCTAT  AAGCTGGTCA
   1080        1090        1100        1110        1120
   CgACAaggcC  AAgCAGGAtG  TCACaGAGGA  GGACTTCTAc  AgGCTaGTCA 1110        1120        1130        1140        1150
        *           *           *           *           *
   GCGGGCTCAC  CGTCACCAAG  GGGCTCAGAG  GTGCCAATGC  CACGTACGAG
   1130        1140        1150        1160        1170
   GtGGAcACAC  TGTCgCCAAG  GGGCTtAAAG  GcACCcAaGC  CACcTTtGAc 1160        1170        1180        1190        1200
        *           *           *           *           *
   GTGTACACCG  AGCCCTGGGC  CCAGGACTCA  TCCCAGGAGA  CCAGGAAGAA
   1180        1190        1200        1210        1220
   AtcTACACTg  AGtCCTGGGC  CCAGGACcCg  TCCCAGGAGA  aCATGAAGAA 1210        1220        1230        1240        1250
        *           *           *           *           *
   GACCATGGTG  GACCTGGAGA  CTGACATCCT  CTTCCTGATC  CCCACAAAGA
   1230        1240        1250        1260        1270
   GACAgTGGTG  GcCTTtGAGA  CTGACATaCT  CTTCCTGATC  CCCACAgAGA 1260        1270        1280        1290        1300
        *           *           *           *           *
   TTGCCGTGGC  CCAGCACAAG  AGCCACGCCA  AGAGCGCCAA  CACCTACACC
                                    G
   1280        1290        :           1310        1320
   TgGCtcTGGC  CCAGCA-cAG  AcCCATGCCA  AGAGtGCCAA  gACCTACtCt 1310        1320        1330        1340        1350
        *           *           *           *           *
   TACCTGTTCT  CCCAACCGTC  TCGGATGCCC  ATCTACCCCA  AGTGGATGGG
```

FIG. 2e

```
1330       1340       1350       1360       1370
TACCTGTTtT CCCAcCCtTC ACGAATGCCt ATCTACCCaA AaTGGATGGG

*1360      *1370      *1380      *1390      *1400
GGCTGACCAC GCCGATGACC TCCAGTATGT CTTCGGGAAG CCCTTCGCCA 1380       1390       1400       1410       1420
GGCAGACCAC GCTGATGACC TCCAGTAcGT CTTtGGGAAG CCCTTtGCCA

*1410      *1420      *1430      *1440      *1450
CCCCCCTGGG CTACCGGGCC CAAGACAGGA CTGTCTCCAA GGCCATGATT 1430       1440       1450       1460       1470
CCCCaCTGGG CTACCGGGCC CAAGACAGGA CTGTCTCCAA GGCCATGATT

*1460      *1470      *1480      *1490      *1500
GCCTACTGGA CCAACTTTGC CAGAACTGGG GACCCTAACA CGGGCCACTC 1480       1490       1500       1510       1520
GCCTACTGGA CCAACTTTGC CAaGAgTGGG GACCCcAACA TGGGCaACTC

*1510      *1520      *1530      *1540      *1550
GACAGTGCCC GCAAACTGGG ATCCCTACAC CCTGGAAGAT GACAACTACC 1530       1540       1550       1560       1570
AcCcGTGCCC ACAcACTGGT AcCCtTATAC CAtGGAgAAT GGtAACTACC

*1560      *1570      *1580      *1590      *1600
TGGAAATCAA CAAGCAGATG GACAGCAACT CTATGAAGCT GCATCTGAGG 1580       1590       1600       1610       1620
TGGAcATCAA TAAGAAAaTA AcCAGCAcCT CcATGAAGGa GCAcCTaAGG

*1610      *1620      *1630      *1640      *1650
ACCAACTACC TGCAGTTCTG GACCCAGACC TACCAGGCCC TGCCCACGGT 1630       1640       1650       1660       1670
GAAAAgTTCC TcAAGTTCTG GgCTGTGACA TTcGAGAtGC TGCCCACtGT
```

FIG. 2f

```
       1660       1670       1680       1690       1700
     *    *     *    *     *    *     *    *     *    *
GACCAGCGCG GGGGCCAGCC TGCTGCCCCC CGAGGACAAC TCTCAGGCCA
     1680       1690        1700       1710
----G-GTTG GTGACCACAC -T---CCCCC TGAGGATGAC TCAGAGGCTG
       1710       1720       1730       1740       1750
     *    *     *    *     *    *     *    *     *    *
GCCCCGTGCC CCCAGCGGAC AACTCCGGGG CTCCCACCGA ACCCTCTGCG
  1720       1730       1740       1750       1760
CCCCCGTCCC ACCTACAGAC GACTCCCAGG GTGGTCCTGT CCCACCTACA
       1760       1770       1780       1790       1800
     *    *     *    *     *    *     *    *     *    *
GGTGACTCTG AGGTGGCTCA GATGCCTGTC GTCATTGGTT TCTAATGTCC
  1770       1780       1790       1800       1810
GATGACTCTC AGACAACACC GGTGC-CCCC AACAGACAAC TCTC-AGGCT
       1810       1820       1830       1840       1850
     *    *     *    *     *    *     *    *     *    *
TTGGCCTCCA GGGGCCACAG GAGACCCAG GGCCCACTTC CCTCCCAAGT
  1820       1830       1840       1850       1860
GGTGAC-TCT GTGGAGG-CT CAGATGCCTG GTCCCATTGG CTTCTAAAG-
       1860       1870       *
     *    *     *    *
GCCTCCTGAA TAAAGCCTCA ACCATCTC(POLY A)
  1870
TCC-TATAAA CCGGGGC
```

PEPTIDES FROM MAMMALIAN PANCREATIC CHOLESTEROL ESTERASE

This is a division of application Ser. No. 08/350,801, filed Dec. 7, 1994, now abandoned, which is a continuation of U.S. application Ser. No. 07/856,910, filed May 12, 1992, now abandoned, which claims priority to PCT/US90/9483, filed Nov. 13, 1990, which in turn is a continuation of U.S. application Ser. No. 07/439,899, filed Nov. 20, 1989, now U.S. Pat. No. 5,100,510.

BACKGROUND OF THE INVENTION

1. Field of the Invention

The invention relates to enzymes involved in the metabolism of cholesterol and more specifically to the cholesterol esterase secreted by the pancreas in mammals. Cholesterol metabolism is of critical interest to those involved in protecting human health. Atherosclerosis is the leading cause of death in the United States and reduction of serum cholesterol levels has recently been embraced as a national health priority. See NIH Consensus Panel Report, J.A.M.A. 253: 2094 (1985). NIH recommendations include measurement of serum cholesterol in all adults, with efforts to reduce cholesterol in those individuals with levels above 200 mg %. In this regard front line therapy is a reduction in the amount of cholesterol and triglycerides ingested, followed by the use of agents that interfere with absorption of ingested lipids. See Consensus Full Report, Arch. Inst. Med. 148: 36 (1988).

Pancreatic cholesterol esterase plays a pivotal role in the absorption of cholesterol and fatty acids. The inhibition of cholesterol esterase could lead to reduced serum cholesterol levels. Numerous approaches to developing inhibitors of cholesterol esterase will likely be attempted, including the use of chemical inhibitors. Therapeutic biologicals, such as monoclonal or polyclonal antibodies to pancreatic cholesterol esterase have great potential. In particular, antibodies against purified cholesterol esterase can be isolated from the milk of immunized cows and used as an ingestible therapeutic. Analogs of pancreatic cholesterol esterase are proteins similar to cholesterol esterase, but with sufficient variation in amino acid sequence to bind cholesterol esters without releasing free cholesterol and fatty acids. If such analogs can be developed they will serve as powerful inhibitors of cholesterol esterase function.

Whatever type of inhibitor is being developed, large quantities of highly purified enzyme are required to test the efficacy of any potential inhibitor, as well as to better understand the enzyme and thus allow the development of further therapeutic means. There is, therefore, a need for methods to purify useful quantities of homogeneous pancreatic cholesterol esterase. In addition, for the preparation of analog inhibitors, the amino acid sequence of the enzyme and its underlying DNA sequence must be known. Thus, there is a need for a cloned DNA sequence encoding cholesterol esterase, from which the DNA and amino acid sequences may be determined.

Finally, pancreatic cholesterol esterase has considerable commercial utility for enzymatic hydrolysis or synthesis of ester linkages in the preparation of biologicals or foodstuffs such as dairy products. There is, therefore, a need for a means of producing commercially significant, large-scale quantities of homogeneous cholesterol esterase, especially from cows, which cannot be met by purification of the enzyme from natural sources. What is needed, then, is a means for producing pancreatic cholesterol esterase through the use of recombinant DNA expression vectors in a suitable host cell or organism, as well as a means of large-scale purification of the enzyme so expressed.

2. Information Disclosure

Borja et al., 1964, Proc. J. Exp. Biol. and Med. 116: 496, teach that cholesterol esterase is secreted by the pancreas, and that its catalysis of cholesterol ester hydrolysis to produce free cholesterol and free fatty acids is essential for the absorption of cholesterol. Bosner et al., 1988, Proc. Natl. Acad. Sci. USA 85: 7438, teach that cholesterol esterase performs its function while anchored to the intestinal membrane via a receptor-like interaction with brush border membrane associated heparin. Lange and Spilburg, in co-pending application U.S. Ser. No. 340,868, teach sulfated polysaccharide inhibitors of human pancreatic cholesterol esterase which are effective in blocking the absorption of cholesterol and fatty acids into intestinal cells.

Numerous procedures for the preparation of pancreatic cholesterol esterase have been reported. See, e.g., Allain et al., 1974, Clin. Chem. 20: 470, Calame et al., 1975, Arch. Biochem. Byophys. 168: 57, Labow et al., 1983, Biochem. Byophys. Acta 749: 32. In general, the reported procedures are tedious and give poor yields of heterogeneous material. Production of significant quantities of homogeneous material has not been achieved. For example, the commercially available cholesterol esterase, prepared by the method of Allain et al., is less than 5% pure according to both physical and functional assays. None of the existing preparative procedures has been useful for purifying cholesterol esterase from several different mammalian species.

BRIEF SUMMARY OF THE INVENTION

The present invention is directed toward the preparation of useful quantities of homogeneous mammalian pancreatic cholesterol esterase. The invention encompasses methods for large-scale purification of pancreatic cholesterol esterase from natural sources or from prokaryotic or eukaryotic cell cultures producing recombinant mammalian pancreatic cholesterol esterase. The invention also comprises mammalian pancreatic cholesterol esterases purified according to such methods, and the use of such purified enzymes to produce and purify antibodies to such enzymes, and to screen potential inhibitors to such enzymes. In addition, the invention comprises the use of such purified enzyme to alter the cholesterol composition of food-stuffs and biologics.

The invention further comprises cloned DNA sequences encoding mammalian pancreatic cholesterol esterase, expression vectors containing such DNA sequences, and prokaryotic or eukaryotic cell cultures harboring said expression vectors, whereby said cell cultures are capable of producing mammalian pancreatic cholesterol esterase. The invention additionally comprises a process for commercial-scale production and purification of mammalian pancreatic cholesterol esterase through the application of the aformentioned purification methods to the supernatants of said mammalian pancreatic cholesterol esterase-producing cell cultures. The invention finally comprises homogeneous mammalian pancreatic cholesterol esterase produced by such a process.

BRIEF DESCRIPTION OF THE DRAWINGS

FIG. 1. The deduced amino acid sequence of bovine pancreatic cholesterol esterase.

FIG. 2. The cDNA sequence of bovine pancreatic cholesterol esterase. The underlined region of the cholesterol esterase cDNA is the complementary sequence of the oligonucleotide probe.

DETAILED DESCRIPTION OF THE INVENTION

Large-scale purification to homogeneity of mammalian pancreatic cholesterol esterase from human, bovine, porcine, and rat pancreas has now been achieved through the use of sulfated matrices in affinity chromatography. This is the first method ever to allow purification of this enzyme from all mammalian species tested. The major form of the enzyme purified from bovine pancreas has a molecular weight of 72 kilodaltons (kDa) and has never before been detected.

The observation that certain sulfated polysaccharides can decrease cholesterol absorption was recently disclosed in co-pending application U.S. Ser. No. 340,868, which is incorporated herein by reference. The sulfated polysaccharides reported in that investigation have the characteristic of binding to mammalian pancreatic cholesterol esterase. Thus, it is possible to use these compounds as an affinity matrix for the purification of pancreatic cholesterol esterase. Pancreatic cholesterol esterase contains a specific sulfate recognition site which allows it to bind to a large number of sulfated compounds which include, but are not limited to, heparin-agarose, Mono S, SP-Sephadex, cellulose sulfate, pectin sulfate, chitin sulfate, chitosan sulfate and 2, 3, or 6-congeners of chitosan sulfate, agar sulfate, amylopectin sulfate and any combination of monomers or polymers of the above. Those skilled in the art will recognize that other polysaccharides or resins may become sulfated through the action of chlorosulfate, sulfur dioxide, or other sulfating agents, whereby, in view of the above, such sulfated polysaccharides or resins could be employed as affinity matrices for the purification of pancreatic cholesterol esterase. Preferably, sulfated polysaccharides are used as the affinity matrix. In particular, sulfated cellulose which has been sulfated to an extent insufficient to make it soluble in water or heparin agarose are most preferred.

The binding of sulfated polysaccharides by pancreatic cholesterol esterase involves one or more specific regions of the protein, one of which in the bovine protein is represented by the amino acid sequence MDGHLFATVDVPAID-KAKQDV. Those skilled in the art will recognize that the sulfate binding sites of the human, porcine, and rat pancreatic cholesterol esterase enzymes, and of mammalian pancreatic cholesterol esterase enzymes will have substantially the same amino acid sequence. Substantially the same amino acid sequence is understood to mean an amino acid sequence in which any amino acid substitutions are conservative and do not significantly affect the function of the protein or any domain or region thereof (e.g., the ability of the region described above to bind to sulfated polysaccharides).

Specific amino acid sequences that bind sulfated agents have been identified by chemical cross-linking between the amino acid sequence and the sulfated agent, followed by cleavage of the protein to obtain the sulfated agent-bound oligopeptide and determination of the amino acid sequence of the oligopeptide. An oligopeptide having the amino acid sequence KKRCLQ has been identified as a binding site for sulfated agents on bovine rat and human cholesterol esterase. Binding of sulfated agents to this site on the enzyme does not inhibit enzyme function. In contrast, the oligopeptide PAINKGNKKV from human pancreatic cholesterol esterase binds sulfated agents in a manner that inhibits enzyme function. This binding site is only partially formed in the rat and bovine cholesterol esterases and comprises, respectively, the amino acid sequence PAIKD-KQDV or PAINSNKQDV. The inhibitory binding sequence is encoded in the human gene by the nucleotide sequence CCTGCCATCAACAAGGGCAACAAGAAAGTC.

Those skilled in the art will recognize that the oligopeptides of the invention are useful in various applications. For example, the oligopeptides may be used in in vitro binding assays to determine their capacity to bind to various sulfated agents. In this way, sulfated agents with a high binding affinity for the oligopeptides, and thus a high potential for binding or binding and inhibiting the enzyme can be identified. Any such sulfated agents would be useful for purifying the enzyme, and those binding the oligopeptide associated with enzyme inhibition will be strong candidates for cholesterol esterase inhibitor development. Thus the oligopeptides of the invention are useful for identifying agents that are useful for purifying or inhibiting pancreatic cholesterol esterase. The oligopeptides of the invention are also useful for therapeutic treatments designed to decrease cholesterol absorption. This is because the oligopeptides are capable of displacing the enzyme from its intestinal cell binding site by competitive binding. Thus the oligopeptides may be incorporated in a pharmaceutically acceptable carrier and administered in an amount effective for reducing cholesterol absorption. Displacement of cholesterol esterase by the oligopeptides may also be useful for enzyme purification purposes by using the oligopeptides to release bound enzyme in affinity chromatography procedures.

Purification of the enzyme takes advantage of the affinity of the enzyme, principally through its sulfate binding site, for a sulfated matrix. A solution comprising the pancreatic cholesterol esterase is applied to the sulfated matrix. The solution must be provided at a salt concentration and pH sufficient to allow the pancreatic cholesterol esterase to bind to the sulfated matrix. A variety of low salt concentrations will allow binding. Most preferably, binding is allowed to occur in 25 mM acetate, 50 mM benzamidine at a pH of 5.1. The use of a buffer at this pH and the presence of benzamidine serve to inhibit proteolysis. Prior art procedures have failed to address the problem of proteolysis during purification. This is believed to be the reason that the major form (72 kDa) of the bovine enzyme has never been detected previously, even though it may be related structurally as a derivative of the previously described 67 kDa bovine enzyme.

After binding of the pancreatic cholesterol esterase to the sulfated matrix has occurred, contaminating proteins can be removed by washing the column with a solution at a salt concentration and pH sufficient to allow continued binding of the pancreatic cholesterol esterase to the sulfated matrix. This may be achieved through the use of either a single wash solution or a linear salt gradient. For example, sulfated resins are preferably washed with linear salt gradients, whereas sulfated polysaccharides, including cellulose-sulfate and heparin-agarose are most preferably washed with a single wash solution at a higher salt concentration because these matrices bind the enzyme with higher affinity. Pancreatic cholesterol esterase is finally eluted from the sulfated matrix by washing the matrix with a solution at a salt concentration and pH sufficient to inhibit the binding of the enzyme to the sulfated matrix. When a linear salt gradient is employed, fractions are collected and the enzyme will be present in fractions at higher salt concentrations. Alternatively, when sulfated polysaccharides are utilized as the affinity matrix, the enzyme can be collected with a single wash utilizing a solution of a sulfated bile salt, such as taurocholate. Preferred sulfated matrices with conditions for binding and elution are described in Example 5. Combinations of matrices can be used for purification to homogeneity and other preliminary steps may be included. The bovine major (72 kDa) species, for example, was purified by the sequential chromatography steps of S-Sepharose with a linear salt gradient. SP-Sephadex with a linear salt gradient and mono-S with a linear salt gradient. Human pancreatic cholesterol esterase, in contrast, was preliminarily fractionated over hydroxylapatite and AcA-34, followed by purification on heparin-sepharose with a single high salt elution step.

The ability to purify to homogeneity significant quantities of mammalian pancreatic cholesterol esterases in general and human pancreatic cholesterol esterase in particular, allows for the first time on a large scale the production of antibodies to human pancreatic cholesterol esterase, as well as to other mammalian pancreatic cholesterol esterases. The homogeneous enzyme is used to immunize cows which produce antibodies to the enzyme and secrete it into their milk. The antibodies are readily purified from the milk by affinity chromatography using a binding component comprising homogeneous pancreatic cholesterol esterase crosslinked to an inert matrix. In this manner large quantities of purified antibodies highly specific for pancreatic cholesterol esterase are readily prepared. Such antibodies, particularly antibodies to human pancreatic cholesterol esterase, can be used as inhibitors to pancreatic cholesterol esterase and might lead to reduced serum cholesterol levels.

FIG. 1 shows the amino acid sequence deduced from the nucleotide sequence shown in FIG. 2 of bovine pancreatic cholesterol esterase. The amino acid sequence in FIG. 1 further enables the production of antibodies to peptides comprising less than a complete pancreatic cholesterol esterase molecule. Such peptides may be prepared by chemical synthesis or by proteolytic or chemical cleavage of the purified enzyme. The peptides may be used alone to immunize cows or may be coupled to a carrier protein, such as keyhole limpet hemocyanin (KLH). In either case the antibodies would be purified from cow's milk using affinity chromatography with the purified enzyme as the binding component, as described above.

The present invention provides, for the first time, useful quantities of homogenous pancreatic cholesterol esterase. Thus the homogeneous enzyme composition can be used to screen potential inhibitors of pancreatic cholesterol esterase for their ability to modify enzyme properties, such as release of free cholesterol from fatty acyl cholesterol esters, or binding of immobilized heparin.

The ability to produce useful quantities of this enzyme in pure form further allows for the use of the enzyme in commercial applications. In particular, the purified enzyme will be used to alter the cholesterol/cholesterol ester composition of foodstuffs and biologics through its catalytic function. The bile salt taurocholate is required at concentrations above 1 mM for esterase activity whereas in the absence of taurocholate or in the presence of low concentrations of taurocholate (i.e., less then 250 µM) the enzyme will operate to esterify cholesterol. Thus, both increases and decreases in free cholesterol in biologics or foodstuffs may be moderated by the same enzyme by simply altering the conditions.

The present invention provides also, for the first time, a composition of homogeneous mammalian pancreatic cholesterol esterase, especially the bovine 72 kDa species, in sufficient quantity for amino acid sequence analysis. Those skilled in the art will recognize that the ability to carry out such an analysis greatly enhances the probability of successfully cloning the gene encoding the underlying peptide sequence. Amino acid sequence determination allows the determination of a finite set of nucleotide sequences which can encode a particular peptide, based upon the genetic code. Within such a finite set of nucleotide sequences will be found a smaller set of nucleotide sequences which are more likely to encode the particular peptide, on the basis of the codon usage preference of the organism from which the gene is to be isolated.

Once a tissue source which expresses the protein of interest has been identified, mRNA can be isolated from this source. The mRNA can be used to synthesize cDNA, from which a library can be prepared. A mixture of oligonucleotides corresponding to the subset of nucleotide sequences most likely to encode a peptide from the protein can then be used to screen the library for the presence of a cDNA encoding the protein of interest.

In the case of mammalian pancreatic cholesterol esterase, the pancreas has long been known in the art as the tissue source expressing this enzyme. We have additionally discovered that expression of this enzyme in the pancreas of adult cows greatly exceeds that of calf pancreas. Thus, mRNA was prepared from adult bovine pancreas by standard procedures, and used for the synthesis of cDNA, according to procedures well known in the art. A cDNA library was prepared by conventional methods.

Conventional N-terminal amino acid sequence analysis of the homogeneous composition of bovine pancreatic cholesterol esterase, prepared as described herein, allowed the synthesis of a mixed oligonucleotide probe of the following sequence:

This probe mixture was shown to hybridize very strongly in Northern blots of mRNA isolated from adult bovine pancreas to an mRNA species of 1.9 kb. No detectable hybridization was observed when mRNA isolated from calf pancreas was used. The probe was then used to identify a hybridizing clone from the cDNA library. The clone was isolated and a plasmid containing a full-length cDNA encoding pancreatic cholesterol esterase was excised therefrom. The nucleotide sequence of the cDNA was determined according to procedures well known in the art. The amino acid sequence for the entire bovine protein is shown in FIG. 1, as deduced from the nucleotide sequence shown in FIG. 2. The predicted peptide sequence is 578 amino acids in length and has a molecular weight of 63.5 kDa in the absence of glycosylation. There are two potential N-glycosylation sites. The theoretical isoelectric point of the unglycosylated protein is 5.1.

The cDNA shown in FIG. 2 was then used as a probe to screen a human pancreatic cDNA library. The bovine probe was hybridized to the human pancreatic cDNA library. Positive clones were obtained, including full length clones. Partial DNA sequence analysis confirmed that the clones encoded human pancreatic cholesterol esterase.

Thus, the present invention encompasses a cloned DNA sequence encoding mammalian pancreatic cholesterol esterase. For purposes of defining this aspect of the invention, a cloned DNA sequence will be interpreted to mean a DNA molecule comprising two portions: a (1) specific nucleotide sequence, covalently attached to (2) another DNA molecule portion which is capable of autonomous replication within a bacterial, yeast, plant, insect or mammalian cell, wherein the autonomously replicating DNA molecule is not a bacterial, yeast, plant, insect or mammalian chromosome, and whereby the cloned DNA sequence and attaches autonomously replicating DNA molecule are capable of replicating autonomously as a unit within a bacterial, yeast, plant, insect or mammalian cell. Thus, a cloned DNA sequence may refer to a cloning vector that contains a specific nucleotide sequence encoding a cholesterol esterase. A DNA sequence encoding mammalian pancreatic cholesterol esterase is defined as a DNA sequence which, when transcribed and translated in a cell will give rise to a protein which is capable of releasing oleic acid from cholesteryl oleate, and is also capable of liberating palmitic acid from palmitoyl lysophosphatidyl choline. A representative DNA sequence encoding a mammalian pancreatic cholesterol esterase is the bovine sequence shown in FIG. 2. Those skilled in the art will recognize that the disclosure relating the cloning of this DNA sequence coupled with the DNA sequence shown in FIG. 2 fully enables the cloning of other mammalian pancreatic cholesterol esterases including those from humans, pigs, and rats. DNA sequences encoding any mammalian pancreatic cholesterol esterase, as defined above are enabled and contemplated by the present invention.

A recombinant expression vector encoding a mammalian pancreatic cholesterol esterase can readily be prepared by methods well known in the art. Such a vector comprises the DNA sequence encoding a mammalian pancreatic cholesterol esterase, a promoter of other DNA sequence recognized by RNA polymerase as a signal for the initiation of transcription, and an origin of replication which allows the vector to replicate in a bacterial, yeast, plant, insect, or mammalian cell.

Cell culture expression systems have been extensively discussed in the art. Most preferred are mammalian cell culture expression systems, particularly the systems involving CHO(dhfr—) cells. In such a system, a recombinant expression vector encoding and capable of expressing the pancreatic cholesterol esterase can be introduced into CHO (dhfr—) cells together with a plasmid encoding and capable of expressing dhfr. Transfected cells can be selected in selective media, for example hypoxanthine-glycine-thymidine (HGT) media. Subsequent amplification of transfected DNA can be mediated by growing transfected cells in media containing methotrexate. Expression may be assayed by activity assays carried out using culture supernatants or through well established immunological procedures.

The following examples are shown by way of illustration and not by way of limitation.

EXAMPLE 1

Purification of Human Pancreatic Cholesterol Esterase

Human pancreas was received at autopsy. About 30 g of tissue in 10 mM phosphate, pH 6.0, 50 mM benzamidine, 0.5% digitonin were homogenized with a polytron, centrifugally pelleted (48,000×g, 30 min.) and the supernatant collected. The supernatant was centrifugally pelleted (100,000×g, 60 min.) again and the second supernatant was passed through glass wool and dialized overnight against 50 mM benzamidine, 10 mM phosphate, pH 6.8. The dialysate was loaded onto a hydroxylapatite column (2.6×10 cm) equilibrated with 50 mM benzamidine, 10 mM phosphate, pH 6.8. The column was washed with identical buffer, then developed with a linear gradient of 50 mM to 350 mM phosphate, pH 6.8, 50 mM benzamidine. The cholesterol esterase activity eluted at a conductivity of 20–22 mS/cm. These fractions were pooled and loaded onto an AcA34 column (Bio-Rad Laboratories, Inc., 2200 Wright Avenue, Richmond, Calif. 94804) (2.6×90 cm) equilibrated with 500 mM NaCl, 10 mM phosphate, pH 6.0. The fraction emerging at an apparent molecular weight of 350 kDa contained cholesterol esterase activity and was dialyzed against 10 mM phosphate, pH 6.0.

The enzyme was applied to heparin Sepharose (Pharmacia Inc., 800 Centennial Avenue, Piscataway, N.J. 08854) equilibrated with the same buffer. The resin was then washed with five to 10 column volumes of 50 mM NaCl, 50 mM benzamidine, 10 mM Tris, pH 7.2 followed by two column volumes of 20 mM taurocholate, 30 mM NaCl, 50 mM benzamidine, 10 mM Tris, pH 7.2. Purified enzyme is then eluted in 500 mM NaCl, 10 mM Tris, pH 7.2, 50 mM benzamidine.

EXAMPLE 2

Purification of Bovine Pancreatic Cholesterol Esterase

Commercially available bovine pancreatic cholesterol esterase (Sigma Chemical Co., P.O. Box 14509, St. Louis, Mo. 63178; purity<1%) in 10 mM Tris, pH 7.2, was applied to heparin-Sepharose (Pharmacia Inc., 800 Centennial Avenue, Piscataway, N.J. 08854) (1.5×10 cm) equilibrated with the same buffer. The resin was developed further by washing with 0.10M NaCl, 10 mM Tris, pH 7.2. Little or no activity was found in any of these preliminary steps, even though virtually all of the applied protein was eluted. When the absorbance at 280 nm returned to zero, the resin was washed with 20 mM sodium taurocholate containing sodium chloride to give a conductivity of 13 to 15 mS/cm, the same conductivity as that of the previous washing buffer. All the activity was eluted in several fractions. This single purification step typically provided a 60 to 80% yield with a 50- to 100-fold purification and gives a single band at 67 kDa on SDS-PAGE. No additional activity was found when the resin was washed with higher concentrations of salt and the resin could be regenerated by washing with 2.0M NaCl, 10 mM Tris, pH 7.2. The large purification factor achieved by this single step indicates that heparin is acting as an affinity ligand for cholesterol esterase, a property demonstrated further by using different elution conditions. Thus, when the charged resin was washed with heparin (2 mg/ml), greater than 95% of the enzyme was eluted from the resin, while chondroitin sulfate (5 mg/ml), another sulfated mucopolysaccharide, removed less than 2% of bound enzyme.

EXAMPLE 3

Purification of Porcine Pancreatic Cholesterol Esterase

The same procedure described in Example 2 for the human enzyme was used for porcine pancreatic cholesterol esterase. In this case, active enzyme was found at 15 to 17 mS/cm from the hydroxylapatite column, and emerged from the AcA 34 gel filtration column (Bio-Rad Laboratories, 2200 Wright Avenue, Richmond, Calif. 94804) at a molecular weight of 81 kDa. This procedure provides homogeneous enzyme with molecular weight 81 kDa in 25% yield.

EXAMPLE 4

Purification of Bovine 72 kDa Major Species Pancreatic Cholesterol Esterase

Supernatant from bovine pancreas homogenate was prepared according to Example 1 as described for the human enzyme. The supernatant was chromatographed over S-Sepharose (Pharmacia Inc., 800 Centennial Avenue, Piscataway, N.J. 08854) in 25 mM acetate pH 5.1, 50 mM benzamidine. The enzyme was eluted from the column using a linear salt gradient from 175 mM NaCl to 500 mM NaCl. The eluate was loaded onto a SP-Sephadex (Pharmacia Inc., 800 Centennial Avenue, Piscataway, N.J. 08854) column in 25 mM acetate, pH 5.1, 50 mM benzanidine, then eluted with a linear gradient of 0 mM to 120 mM NaCl. The eluate contained two bands exhibiting cholesterol esterase activity, one at 72 kDa (90–99%) and one at 67 kDa (1–10%). The 72 kDa form was completely separated from the 67 kDa form by chromatography over a mono-S column (Pharmacia Inc., 800 Centennial Avenue, Piscataway, N.J. 08854).

EXAMPLE 5

Purification of Cholesterol Esterases Using Sulfated Cellulose Columns

A. Preparation of Sulfated Cellulose Columns

Cellulose was lightly sulfated to maintain its insolubility and this material was used as a potent matrix for isolating and purifying the enzyme. Thus, 2.5 g of cellulose (type 100) was suspended in 50 ml water and 12.5 g of sulfur trioxide pyridine complex were added with stirring. After one hour at room temperature, 100 ml of dimethylformamide were added, and the mixture was stirred for an additional 30 minutes. The cellulose sulfate was collected by centrifugation. After washing six times with water, the resin was packed in a small column (0.9×9 cm).

Resins such as those described in part A of this example and the other sulfated polysaccharides can be used to purify cholesterol esterases. For example, bovine cholesterol esterase was pumped onto the resin in 25 mM acetate, pH 5.1 at 15 ml/hr. All the activity was bound, but in this case, binding was so strong that even 2M NaCl in 25 mM acetate, pH 5.1 did not remove the enzyme. Elution with 100 mM taurocholate, a sulfated bile salt, removed all the activity in virtually 100% yield. Heparin agarose also functions as an effective affinity matrix for cholesterol esterase in the same manner.

EXAMPLE 6

Assays for Cholesterol Esterase Activity

Cholesterol esterase activity was determined by measuring the release of [$^{14}$C]-oleic acid from vesicles containing cholesteryl 1-[$^{14}$C]-oleate. Vesicles were prepared by drying under nitrogen a solution of 1.00 ml of 1.33 mM egg phosphatidylcholine in hexane and 1.27 ml of 1 mM cholesteryl oleate containing 10 µl of cholesteryl 1-[$^{14}$C]-oleate (2.2×10$^5$ cpm) in chloroform. The precipitate was resuspended in 10 ml of 0.15M Tris, pH 7.5, vortexed vigorously for several seconds and then sonicated on ice for 20 minutes under nitrogen. Following sonication, the preparation was centrifuged at 48,000×g for 60 minutes, and the vesicle preparation was carefully decanted and stored at 4° C. In a typical assay, 75 µl of cholesteryl [$^{14}$C]-oleate vesicles, 25 µl of 100 mM taurocholate, 175 µl of 0.15M Tris, pH 7.5 were mixed in a test tube and hydrolysis was initiated by adding 25 µl of enzyme to the reaction mixture at 37° C. After a known time, usually five minutes, the reaction was quenched by addition of 600 µl of 0.3N NaOH and 3 ml of benzene:methanol:chloroform (1:1.2:0.5). After mixing, the samples were centrifuged and 1 ml of the clear organic phase was removed and counted for radioactivity. Since only part of the sample was removed for counting, an efficiency sample was prepared by adding 100 µl of [$^{14}$C]-oleic acid vesicles of known specific radioactivity to 200 µl of 0.15M Tris, pH 7.5. The same manipulations were performed on this sample as those described above for assay. The efficiency of transfer was then determined by dividing the number of counts in the 1 ml organic phase by the dpm in 100 µl of starting [$^{14}$C]-oleic acid vesicles. Activity is expressed as nanomoles of oleic acid released/ml/hour and was less than 0.1 nmol/ml/hr in the absence of added enzyme. To assess the potential inhibition of chemical compounds, these agents are added to the incubation mixture before addition of cholesterol esterase and the ratio of [$^{14}$C]-oleate release determined as above and compared to the ratio observed in the absence of the test compound.

EXAMPLE 7

Preparation of Rabbit IgG Fraction Against 67 kDa Bovine Pancreatic Cholesterol Esterase Five hundred micrograms of homogenous 67 kDa protein were emulsified in Freund's complete adjuvant (CFA) and injected subcutaneously into a New Zealand White rabbit. Twenty-one days later the rabbit was boosted with intraperitoneal injections of 250 µg protein dissolved in 1 ml of 10 mM sodium phosphate, 150 mM NaCl, pH 7.1. The rabbits were bled 10 days later and the presence of anti-cholesterol IgG was determined on Ouchterlony plates. Rabbit IgG was purified by passing 20 ml of rabbit serum over a protein A Sepharose (Pharmacia, Inc., 800 Centennial Avenue, Piscataway, N.J. 08854) column equilibrated with 20 mM Tris, 20 mM NaCl, pH 8.0. The resin was washed with equilibration buffer followed by 20 mM Tris, 0.5% deoxycholate, 500 mM NaCl, pH 8.0 and then equilibration buffer. Finally, the IgG was eluted with 100 mM glycine pH 2.8. Similarly, 2 mg of homnogeneous human cholesterol esterase emulsified in CFA are injected into four subcutaneous sites in a cow, and booster injections of 1 mg protein at three and six weeks are made. Secretory antibodies are elicited in the cow's milk that are directed at human cholesterol esterase and can be separated from other milk proteins by ammonium sulfate precipitation and ion-exchange chromatography.

EXAMPLE 8

Construction and Screening of Bovine Pancreas cDNA Library

A. Construction of Bovine Pancreas cDNA Library

Total RNA was extracted from bovine pancreas with 5.5M guanidine thiocyanate, as described by Han et al., 1987, Biochemistry 26: 1617–1625; poly A$^+$ RNA was purified from total RNA by chromatography on oligo dT-cellulose (Pharmacia Inc., 800 Centennial Avenue, Piscataway, N.J. 08854). A cDNA library was constructed using 5 µg of twice-selected poly A$^+$ RNA using a Pharmacia cDNA synthesis kit according to the method of Gubler and Hoffman, 1983, Gene 25: 263–269. The EcoRI-ended double-stranded cDNA was ligated into EcoRI-digested and dephosphorylated λ-ZAP vector arms (Stratagene, 11099 North Torrey Pines Road, La Jolla, Calif. 92037), and packaged using a Stratagene kit. About 300,000 to 500,000 independent, recombinant clones were obtained.

B. Preparation of Probe for Screening the cDNA Library

Total RNA and poly A$^+$ RNA were isolated from pancreas of adult cow or calf as described in part A of this example.

RNA was denatured with formaldehyde and formamide and electrophoresed on a 1% agarose-formaldehyde gel containing 2.2M formaldehyde. RNA was transferred by capillary action to a nylon membrane (Schleicher and Schuell, Inc., 10 Optical Avenue, Keene, N.H. 03431) in 20×SSPE. A 30-mer probe mixture was synthesized based upon N-terminal amino acid sequence determined from purified bovine pancreatic cholesterol esterase. The probe mixture:

```
            A
5'-  GCCTTCCACAAAGCCGCCTTCGGTATACAC- 3'
       T    C         G      C      G
       C
``` was labelled using α-[$^{32}$P]-ATP and polynucleotide kinase. The probe mixture hybridized strongly to a single 1.9 kb band in lanes containing total RNA or poly A$^+$ RNA from adult bovine pancreas, but did not hybridize to lanes containing total RNA or poly A$^+$ RNA from calf pancreas.

C. Screening Bovine Pancreas cDNA Library

The radiolabelled probe described in part B of this example was used to probe the cDNA library constructed as described in part A of this example. The library was screened by plaque hybridization in the presence of 0.25% nonfat dry milk in 6×SSPE. Prehybridization and hybridization were conducted at 60° C. A bluescript plasmid was excised from the hybridizing λ-Zap clones by co-infecting XLI-Blue cells with positive λ-Zap phage and R-408 helper phage. Excision from the plasmid of a cDNA clone encoding the entire cholesterol esterase protein was performed, with identification in the cDNA sequence of both the N-terminal protein sequence and the sequence of the 30-mer probe given in part B of this example. Bluescript plasmids were harvested by the alkaline lysis method of Birnboin, 1983, Meth. Enzymol. 100: 243–255.

EXAMPLE 9

DNA Sequence Analysis of cDNA for Cholesterol Esterase

Each sequencing reaction used approximately 3 μg of double-stranded pBluescript plasmid with positive inserts and 50 ng of sequencing primer. Double-stranded plasmid was denatured for 5 minutes at room temperature with 0.2M NaOH, 0.2 mM ethylene diamine tetraacetate (EDTA) (final concentrations); DNA was precipitated with 0.18M ammonium acetate, pH 5.4 (final concentration) and 2.5 volumes of ethanol. The mixture was chilled on dry ice for 10 minutes and the DNA pellet was spun down for 10 minutes in a microfuge. The pellets were washed with 70% ethanol and vacuum dried. The inserts were sequenced by the dideoxy chain termination method of Sanger et. al., 1977, Proc. Natl. Acad. Sci. USA 74: 5463–5467 using Sequenase™ 2.0 (U.S. Biochemical Corporation, P. O. Box 22400, Cleveland, Ohio 44122) or AMV reverse transcriptase sequencing kit (Stratagene, 11099 North Torrey Pines Road, La Jolla, Calif. 92037). Internal sequences for both strands were obtained by sequential nested primers, 18 to 20 nucleotides in length. The DNA sequence thus obtained is shown in FIG. 2.

EXAMPLE 10

Construction of Expression Vectors

The eukaryotic-prokaryotic shuttle vector pSV2neo has been described by Southern and Berg, (1982) J. Mol. App. Genet. 2: 327–341. A vector capable of expressing bovine pancreatic cholesterol esterase in mammalian cells is prepared by inserting the full-length cDNA (FIG. 2) isolated as described in Example 8, into pSV2neo in such a way as to replace the neo gene, and thus be flanked by the SV-40 early promoter upstream and the SV-40 polyadenylation signal downstream. The insert in the cDNA clone is first site-directed mutagenized to remove a single EcoRI restriction site within the cDNA and then the insert is removed by digesting the cDNA clone with EcoRI. The 1.9 kb insert is isolated by electroelution. The EcoRI ends are converted to blunt ends by incubation of the DNA fragment in the presence of Klenow polymerase and 10 μm dNTPS for 5 minutes. The neo gene is removed from pSV2neo by digestion with HindIII and SmaI and the 4.4 kb vector fragment is isolated by electroelution. The HindIII end is converted to a blunt end using Klenow polymerase. The isolated and blunt-ended fragments are then digested together by the use of T4 DNA ligase and T4RNA ligase (10:1 unit ratio) in the presence of 100 μm ATP and 50 mM MgCl$_2$ at room temperature for about three hours. A portion of the ligation mixture is used to transform competent HB101 *E. coli* bacteria, which are selected for ampicillin resistance. The orientation of the insert is determined by DNA sequencing, as described in Example 9.

EXAMPLE 11

Expression of Bovine Pancreatic Cholesterol Esterase in CHO Cells

The expression vector described in Example 10 is co-introduced into DHFR deficient CHO cells along with a plasmid expressing the DHFR gene, by the method of Graham and Van der Eb, 1973, J. Virology 52: 456–467. The plasmid expressing DHFR is prepared as described in Example 10, except that the DHFR gene from the plasmid pE342.HBV.E400.D22 is used in place of the bovine pancreatic cholesterol esterase gene. The plasmid pE342.HBV.E400.D22 is described in U.S. Pat. No. 4,850, 330. Transfected cells are selected in HGT medium. Resistant colonies are tested for expression of pancreatic cholesterol esterase by collecting their media supernatants and utilizing them in the assay described in Example 6. Clones found to be expressing cholesterol esterase are seeded at 200,000 cells per 100 nM plate in 50 mM methotrexate (MTX) to select for DNA amplification. Cells surviving the initial MTX selection are tested again for cholesterol esterase activity. Those cells showing an increase in cholesterol esterase activity, relative to pre-amplification activity levels, are then furter selected for amplification in 500 nM MTX. Resistant cells showing additional increases in cholesterol esterase activity are finally selected for optimum amplification in 10,000 nM MTX. Those subclones resistant to 10,000 nM MTX which produce the highest levels of cholesterol esterase activity are used as producer cell lines to provide cholesterol esterase which, after purification as described in Example 4, can be used to screen for enzyme inhibitors, produce anti-enzyme antibodies or alter the cholesterol/cholesterol ester composition of foodstuffs.

EXAMPLE 12

Synthesis of Cholesterol Esters by Cholesterol Esterase

Bovine pancreatic cholesterol esterase was incubated at pH 6.0 with 900 μm $^{14}$C-oleate and 700 μm cholesterol or with cholesteryl-[$^{14}$C]-oleate, at varying concentrations of the bile salt taurocholate. Ester synthesis in the former case was assayed by determining the rate of formation of cholesteryl-[$^{14}$C]-oleate and in the latter case as described in Example 6. The synthesis and hydrolytic rates and the ratios between them at various concentrations of taurocholate are shown below in Table I. Rates are expressed as μmoles of product formed per mg of enzyme per hour.

TABLE I

| | Taurocholate, mM | | | |
|---|---|---|---|---|
| | 0 | 0.1 | 1.0 | 10.0 |
| Synthetic | 0.83 | 14.2 | 32.5 | 78.3 |
| Hydrolytic | 0 | 0 | 12.0 | 73.5 |
| Ratio+ | — | — | 2.7 | 1.1 |

These results indicate that the enzyme can be made to act primarily as a synthetic enzyme at appropriate concentrations of taurocholate below 1 mM. Thus, the enzyme can be used to alter the cholesterol/cholesterol ester composition of a given solution by simply adding enzyme and adjusting the level of taurocholate from 0 to 1 mM. Above 1 mM taurocholate, the enzyme is useful for the general hydrolysis of cholesterol esters. Thus, free cholesterol in foodstuffs such as liquid dairy products can be converted into esterified cholesterol, which may be more poorly absorbed than free cholesterol or whose absorption may be inhibited through the oral ingestion of sulfated polysaccharides (see, for example, U.S. Ser. No. 340,868, U.S. Ser. No. 425,109 and co-pending U.S. application entitled, "The Use of Sulfated Polysaccharides To Decrease Cholesterol and Fatty Acid Absorption", filed Oct. 31, 1989, all of which are hereby incorporated by reference).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An oligopeptide comprising the amino acid sequence KKRCLW (SEQ ID NO:11), wherein the oligopeptide is capable of binding sulfated agents that bind to, but do not inhibit mammalian pancreatic cholesterol esterase and wherein said oligopeptide is not an enzyme.

2. An oligopeptide comprising the amino acid sequence PAINKGNKKV (SEQ ID NO:6), wherein the oligopeptide is capable of binding sulfated agents that bind to human pancreatic cholesterol esterase and wherein said oligopeptide is not an enzyme.

* * * * *

UNITED STATES PATENT AND TRADEMARK OFFICE
CERTIFICATE OF CORRECTION

PATENT NO. : 5,792,832
DATED : Aug. 11, 1998
INVENTOR(S) : Louis G. Lange, III et al It is certified that error appears in the above-identified patent and that said Letters Patent is hereby corrected as shown below:

On the title page: Item [63]

"Related U.S. Application Data" delete "439,899, Nov. 20, 1989, Pat. No. 5,100,510" and replace with -- 434,899, Nov. 13, 1989, Pat. No. 5,173,408--

Signed and Sealed this

Fifth Day of January, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 597 amino acids
( B ) TYPE: amino acid
( D ) TOPOLOGY: linear ( i i ) MOLECULE TYPE: protein ( i x ) FEATURE:
( A ) NAME/KEY: misc_feature
( B ) LOCATION: 1..597
( D ) OTHER INFORMATION: /note= "Bovine pancreatic cholesterol esterase"

( x i ) SEQUENCE DESCRIPTION: SEQ ID NO:1:

```
Leu Gly Ala Ser Arg Leu Gly Pro Ser Pro Gly Cys Leu Ala Val Ala
 1               5                  10                  15

Ser Ala Ala Lys Leu Gly Ser Val Tyr Thr Glu Gly Gly Phe Val Glu
                20                  25                  30

Gly Val Asn Lys Lys Leu Ser Leu Phe Gly Asp Ser Val Asp Ile Phe
            35                  40                  45

Lys Gly Ile Pro Phe Ala Ala Ala Pro Lys Ala Leu Glu Lys Pro Glu
    50                  55                  60

Arg His Pro Gly Trp Gln Gly Thr Leu Lys Ala Lys Ser Phe Lys Lys
65                  70                  75                  80

Arg Cys Leu Gln Ala Thr Leu Thr Gln Asp Ser Thr Tyr Gly Asn Glu
                85                  90                  95

Asp Cys Leu Tyr Leu Asn Ile Trp Val Pro Gln Gly Arg Lys Glu Val
                100                 105                 110

Ser His Asp Leu Pro Val Met Ile Trp Ile Tyr Gly Gly Ala Phe Leu
        115                 120                 125

Met Gly Ala Ser Gln Gly Ala Asn Phe Leu Ser Asn Tyr Leu Tyr Asp
    130                 135                 140

Gly Glu Glu Ile Ala Thr Arg Gly Asn Val Ile Val Val Thr Phe Asn
145                 150                 155                 160
```

| | | | | | | | | | | | | | | |
|---|---|---|---|---|---|---|---|---|---|---|---|---|---|---|
| Tyr | Arg | Val | Gly | Pro 165 | Leu | Gly | Phe | Leu | Ser 170 | Thr | Gly | Asp | Ser | Asn 175 | Leu |
| Pro | Gly | Asn | Tyr 180 | Gly | Leu | Trp | Asp | Gln 185 | His | Met | Ala | Ile | Ala 190 | Trp | Val |
| Lys | Arg | Asn 195 | Ile | Glu | Ala | Phe | Gly 200 | Gly | Asp | Pro | Asp | Asn 205 | Ile | Thr | Leu |
| Phe | Gly 210 | Glu | Ser | Ala | Gly | Gly 215 | Ala | Ser | Val | Ser | Leu 220 | Gln | Thr | Leu | Ser |
| Pro 225 | Tyr | Asn | Lys | Gly | Leu 230 | Ile | Lys | Arg | Ala | Ile 235 | Ser | Gln | Ser | Gly | Val 240 |
| Gly | Leu | Cys | Pro | Trp 245 | Ala | Ile | Gln | Gln | Asp 250 | Pro | Leu | Phe | Trp | Ala 255 | Lys |
| Arg | Ile | Ala | Glu 260 | Lys | Val | Gly | Cys | Pro 265 | Val | Asp | Asp | Thr | Ser 270 | Lys | Met |
| Ala | Gly | Cys 275 | Leu | Lys | Ile | Thr | Asp 280 | Pro | Arg | Ala | Leu | Thr 285 | Leu | Ala | Tyr |
| Lys | Leu 290 | Pro | Leu | Gly | Ser | Thr 295 | Glu | Tyr | Pro | Lys | Leu 300 | His | Tyr | Leu | Ser |
| Phe 305 | Val | Pro | Val | Ile | Asp 310 | Gly | Asp | Phe | Ile | Pro 315 | Asp | Asp | Pro | Val | Asn 320 |
| Leu | Tyr | Ala | Asn | Ala 325 | Ala | Asp | Val | Asp | Tyr 330 | Ile | Ala | Gly | Thr | Asn 335 | Asp |
| Met | Asp | Gly | His 340 | Leu | Phe | Val | Gly | Met 345 | Asp | Val | Pro | Ala | Ile 350 | Asn | Ser |
| Asn | Lys | Gln 355 | Asp | Val | Thr | Glu | Glu 360 | Asp | Phe | Tyr | Lys | Leu 365 | Val | Ser | Gly |
| Leu | Thr 370 | Val | Thr | Lys | Gly | Leu 375 | Arg | Gly | Ala | Asn | Ala 380 | Thr | Tyr | Glu | Val |
| Tyr 385 | Thr | Glu | Pro | Trp | Ala 390 | Gln | Asp | Ser | Ser | Gln 395 | Glu | Thr | Arg | Lys | Lys 400 |
| Thr | Met | Val | Asp | Leu 405 | Glu | Thr | Asp | Ile | Leu 410 | Phe | Leu | Ile | Pro | Thr 415 | Lys |
| Ile | Ala | Val | Ala | Gln 420 | His | Lys | Ser | His | Ala 425 | Lys | Ser | Ala | Asn 430 | Thr | Tyr |
| Thr | Tyr | Leu 435 | Phe | Ser | Gln | Pro | Ser 440 | Arg | Met | Pro | Ile | Tyr 445 | Pro | Lys | Trp |
| Met | Gly 450 | Ala | Asp | His | Ala | Asp 455 | Asp | Leu | Gln | Tyr | Val 460 | Phe | Gly | Lys | Pro |
| Phe 465 | Ala | Thr | Pro | Leu | Gly 470 | Tyr | Arg | Ala | Gln | Asp 475 | Arg | Thr | Val | Ser | Lys 480 |
| Ala | Met | Ile | Ala | Tyr 485 | Trp | Thr | Asn | Phe | Ala 490 | Arg | Thr | Gly | Asp | Pro 495 | Asn |
| Thr | Gly | His | Ser 500 | Thr | Val | Pro | Ala | Asn 505 | Trp | Asp | Pro | Tyr | Thr 510 | Leu | Glu |
| Asp | Asp | Asn 515 | Tyr | Leu | Glu | Ile | Asn 520 | Lys | Gln | Met | Asp | Ser 525 | Asn | Ser | Met |
| Lys | Leu 530 | His | Leu | Arg | Thr | Asn 535 | Tyr | Leu | Gln | Phe | Trp 540 | Thr | Gln | Thr | Tyr |
| Gln | Ala | Leu | Pro | Thr | Val 550 | Thr | Ser | Ala | Gly | Ala 555 | Ser | Leu | Leu | Pro | Pro 560 |
| Glu 545 | Asp | Asn | Ser | Gln 565 | Ala | Ser | Pro | Val | Pro 570 | Pro | Ala | Asp | Asn | Ser 575 | Gly |
| Ala | Pro | Thr | Glu 580 | Pro | Ser | Ala | Gly | Asp 585 | Ser | Glu | Val | Ala | Gln 590 | Met | Pro |

Val Val Ile Gly Phe
            595

( 2 ) INFORMATION FOR SEQ ID NO:2:

( i ) SEQUENCE CHARACTERISTICS:
        ( A ) LENGTH: 1908 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 100..129
        ( D ) OTHER INFORMATION: /note= "complementary sequence to
            oligonucleotide probe"

( i x ) FEATURE:
        ( A ) NAME/KEY: CDS
        ( B ) LOCATION: 1..1824

( i x ) FEATURE:
        ( A ) NAME/KEY: misc_feature
        ( B ) LOCATION: 1..1908
        ( D ) OTHER INFORMATION: /note= "Bovine pancreatic
            cholesterol esterase cDNA"

( i x ) FEATURE:
        ( A ) NAME/KEY: sig_peptide
        ( B ) LOCATION: 1..30

( i x ) FEATURE:
        ( A ) NAME/KEY: mat_peptide
        ( B ) LOCATION: 31..1821

( x i ) SEQUENCE DESCRIPTION: SEQ ID NO:2:

```
GCC  TAG  AGG  CAG  ACA  CTG  ACT  ATG  GGG  CGG  CTG  GGA  GCT  AGC  CGT  CTT        48
Ala   *   Arg  Gln  Thr  Leu  Thr  Met  Gly  Arg  Leu  Gly  Ala  Ser  Arg  Leu
-10             -5                         1                       5

GGG  CCG  TCG  CCT  GGC  TGC  TTG  GCA  GTA  GCG  AGT  GCA  GCG  AAG  TTG  GGC        96
Gly  Pro  Ser  Pro  Gly  Cys  Leu  Ala  Val  Ala  Ser  Ala  Ala  Lys  Leu  Gly
               10                       15                      20

TCC  GTA  TAC  ACC  GAA  GGC  GGC  TTC  GTG  GAG  GGC  GTC  AAC  AAG  AAG  CTG       144
Ser  Val  Tyr  Thr  Glu  Gly  Gly  Phe  Val  Glu  Gly  Val  Asn  Lys  Lys  Leu
          25                        30                      35

AGC  CTC  TTT  GGC  GAC  TCT  GTT  GAC  ATC  TTC  AAG  GGC  ATC  CCC  TTC  GCT       192
Ser  Leu  Phe  Gly  Asp  Ser  Val  Asp  Ile  Phe  Lys  Gly  Ile  Pro  Phe  Ala
     40                       45                      50

GCC  GCC  CCC  AAG  GCC  CTG  GAG  AAG  CCC  GAG  CGA  CAC  CCC  GGC  TGG  CAA       240
Ala  Ala  Pro  Lys  Ala  Leu  Glu  Lys  Pro  Glu  Arg  His  Pro  Gly  Trp  Gln
55                       60                      65                      70

GGG  ACC  CTG  AAG  GCC  AAG  AGC  TTT  AAG  AAA  CGG  TGC  CTG  CAG  GCC  ACG       288
Gly  Thr  Leu  Lys  Ala  Lys  Ser  Phe  Lys  Lys  Arg  Cys  Leu  Gln  Ala  Thr
                    75                       80                     85

CTC  ACG  CAG  GAC  AGC  ACC  TAC  GGA  AAT  GAA  GAC  TGC  CTC  TAC  CTC  AAC       336
Leu  Thr  Gln  Asp  Ser  Thr  Tyr  Gly  Asn  Glu  Asp  Cys  Leu  Tyr  Leu  Asn
               90                       95                     100

ATC  TGG  GTC  CCC  CAG  GGC  AGG  AAG  GAA  GTC  TCC  CAC  GAC  CTG  CCC  GTC       384
Ile  Trp  Val  Pro  Gln  Gly  Arg  Lys  Glu  Val  Ser  His  Asp  Leu  Pro  Val
          105                      110                     115

ATG  ATC  TGG  ATC  TAT  GGA  GGC  GCC  TTC  CTC  ATG  GGG  GCC  AGC  CAA  GGG       432
Met  Ile  Trp  Ile  Tyr  Gly  Gly  Ala  Phe  Leu  Met  Gly  Ala  Ser  Gln  Gly
     120                      125                     130

GCC  AAC  TTT  CTC  AGC  AAC  TAC  CTC  TAC  GAC  GGG  GAG  GAG  ATT  GCC  ACA       480
Ala  Asn  Phe  Leu  Ser  Asn  Tyr  Leu  Tyr  Asp  Gly  Glu  Glu  Ile  Ala  Thr
135                      140                     145                     150
```

| | | | | | | | | | | | | | | | | |
|---|---|---|---|---|---|---|---|---|---|---|---|---|---|---|---|---|
| CGG | GGC | AAC | GTC | ATC | GTG | GTC | ACG | TTC | AAC | TAC | CGC | GTT | GGG | CCC | CTG | 528 |
| Arg | Gly | Asn | Val | Ile<br>155 | Val | Val | Thr | Phe | Asn<br>160 | Tyr | Arg | Val | Gly | Pro<br>165 | Leu | |
| GGC | TTT | CTC | AGC | ACC | GGG | GAC | TCC | AAC | CTG | CCA | GGT | AAC | TAT | GGC | CTT | 576 |
| Gly | Phe | Leu | Ser<br>170 | Thr | Gly | Asp | Ser | Asn<br>175 | Leu | Pro | Gly | Asn | Tyr<br>180 | Gly | Leu | |
| TGG | GAT | CAG | CAC | ATG | GCC | ATT | GCT | TGG | GTG | AAG | AGG | AAC | ATT | GAG | GCC | 624 |
| Trp | Asp | Gln<br>185 | His | Met | Ala | Ile | Ala<br>190 | Trp | Val | Lys | Arg | Asn<br>195 | Ile | Glu | Ala | |
| TTC | GGA | GGA | GAC | CCC | GAC | AAC | ATC | ACC | CTC | TTT | GGG | GAG | TCG | GCC | GGA | 672 |
| Phe | Gly<br>200 | Gly | Asp | Pro | Asp | Asn<br>205 | Ile | Thr | Leu | Phe | Gly<br>210 | Glu | Ser | Ala | Gly | |
| GGC | GCC | AGC | GTC | TCT | CTG | CAG | ACC | CTC | TCT | CCC | TAC | AAC | AAG | GGC | CTC | 720 |
| Gly<br>215 | Ala | Ser | Val | Ser | Leu<br>220 | Gln | Thr | Leu | Ser | Pro<br>225 | Tyr | Asn | Lys | Gly | Leu<br>230 | |
| ATC | AAG | CGA | GCC | ATC | AGC | CAG | AGT | GGA | GTG | GGT | TTG | TGC | CCT | TGG | GCC | 768 |
| Ile | Lys | Arg | Ala | Ile<br>235 | Ser | Gln | Ser | Gly | Val<br>240 | Gly | Leu | Cys | Pro | Trp<br>245 | Ala | |
| ATC | CAG | CAG | GAC | CCC | CTC | TTC | TGG | GCT | AAA | AGG | ATT | GCA | GAG | AAG | GTG | 816 |
| Ile | Gln | Gln | Asp<br>250 | Pro | Leu | Phe | Trp | Ala<br>255 | Lys | Arg | Ile | Ala | Glu<br>260 | Lys | Val | |
| GGC | TGC | CCC | GTG | GAC | GAC | ACC | AGC | AAG | ATG | GCT | GGG | TGT | CTG | AAG | ATC | 864 |
| Gly | Cys | Pro<br>265 | Val | Asp | Asp | Thr | Ser<br>270 | Lys | Met | Ala | Gly | Cys<br>275 | Leu | Lys | Ile | |
| ACT | GAC | CCC | CGT | GCC | CTG | ACG | CTG | GCC | TAT | AAG | CTG | CCC | CTG | GGA | AGC | 912 |
| Thr | Asp | Pro<br>280 | Arg | Ala | Leu | Thr | Leu<br>285 | Ala | Tyr | Lys | Leu | Pro<br>290 | Leu | Gly | Ser | |
| ACG | GAA | TAC | CCC | AAG | CTG | CAC | TAT | CTG | TCC | TTC | GTC | CCC | GTC | ATC | GAT | 960 |
| Thr<br>295 | Glu | Tyr | Pro | Lys | Leu<br>300 | His | Tyr | Leu | Ser | Phe<br>305 | Val | Pro | Val | Ile | Asp<br>310 | |
| GGA | GAC | TTC | ATC | CCT | GAT | GAC | CCC | GTC | AAC | CTG | TAC | GCC | AAC | GCC | GCG | 1008 |
| Gly | Asp | Phe | Ile | Pro<br>315 | Asp | Asp | Pro | Val | Asn<br>320 | Leu | Tyr | Ala | Asn | Ala<br>325 | Ala | |
| GAC | GTC | GAC | TAC | ATA | GCG | GGC | ACC | AAT | GAC | ATG | GAC | GGC | CAC | CTC | TTT | 1056 |
| Asp | Val | Asp | Tyr<br>330 | Ile | Ala | Gly | Thr | Asn<br>335 | Asp | Met | Asp | Gly | His<br>340 | Leu | Phe | |
| GTC | GGG | ATG | GAC | GTG | CCA | GCC | ATC | AAC | AGC | AAC | AAA | CAG | GAC | GTC | ACG | 1104 |
| Val | Gly | Met<br>345 | Asp | Val | Pro | Ala | Ile<br>350 | Asn | Ser | Asn | Lys | Gln<br>355 | Asp | Val | Thr | |
| GAG | GAG | GAC | TTC | TAT | AAG | CTG | GTC | AGC | GGG | CTC | ACC | GTC | ACC | AAG | GGG | 1152 |
| Glu | Glu | Asp<br>360 | Phe | Tyr | Lys | Leu | Val<br>365 | Ser | Gly | Leu | Thr | Val<br>370 | Thr | Lys | Gly | |
| CTC | AGA | GGT | GCC | AAT | GCC | ACG | TAC | GAG | GTG | TAC | ACC | GAG | CCC | TGG | GCC | 1200 |
| Leu<br>375 | Arg | Gly | Ala | Asn | Ala<br>380 | Thr | Tyr | Glu | Val | Tyr<br>385 | Thr | Glu | Pro | Trp | Ala<br>390 | |
| CAG | GAC | TCA | TCC | CAG | GAG | ACC | AGG | AAG | AAG | ACC | ATG | GTG | GAC | CTG | GAG | 1248 |
| Gln | Asp | Ser | Ser | Gln<br>395 | Glu | Thr | Arg | Lys | Lys<br>400 | Thr | Met | Val | Asp | Leu<br>405 | Glu | |
| ACT | GAC | ATC | CTC | TTC | CTG | ATC | CCC | ACA | AAG | ATT | GCC | GTG | GCC | CAG | CAC | 1296 |
| Thr | Asp | Ile | Leu | Phe<br>410 | Leu | Ile | Pro | Thr | Lys<br>415 | Ile | Ala | Val | Ala<br>420 | Gln | His | |
| AAG | AGC | CAC | GCC | AAG | AGC | GCC | AAC | ACC | TAC | ACC | TAC | CTG | TTC | TCC | CAA | 1344 |
| Lys | Ser | His | Ala<br>425 | Lys | Ser | Ala | Asn | Thr<br>430 | Tyr | Thr | Tyr | Leu | Phe<br>435 | Ser | Gln | |
| CCG | TCT | CGG | ATG | CCC | ATC | TAC | CCC | AAG | TGG | ATG | GGG | GCT | GAC | CAC | GCC | 1392 |
| Pro | Ser | Arg | Met<br>440 | Pro | Ile | Tyr | Pro | Lys<br>445 | Trp | Met | Gly | Ala | Asp<br>450 | His | Ala | |
| GAT | GAC | CTC | CAG | TAT | GTC | TTC | GGG | AAG | CCC | TTC | GCC | ACC | CCC | CTG | GGC | 1440 |
| Asp | Asp | Leu | Gln<br>455 | Tyr | Val | Phe | Gly | Lys<br>460 | Pro | Phe | Ala | Thr | Pro<br>465 | Leu | Gly<br>470 | |

-continued

| | | | | | | | | | | | | | | | | |
|---|---|---|---|---|---|---|---|---|---|---|---|---|---|---|---|---|
| TAC | CGG | GCC | CAA | GAC | AGG | ACT | GTG | TCC | AAG | GCC | ATG | ATT | GCC | TAC | TGG | 1488 |
| Tyr | Arg | Ala | Gln<br>475 | Asp | Arg | Thr | Val | Ser<br>480 | Lys | Ala | Met | Ile | Ala<br>485 | Tyr | Trp | |
| ACC | AAC | TTT | GCC | AGA | ACT | GGG | GAC | CCT | AAC | ACG | GGC | CAC | TCG | ACA | GTG | 1536 |
| Thr | Asn | Phe | Ala<br>490 | Arg | Thr | Gly | Asp | Pro<br>495 | Asn | Thr | Gly | His | Ser<br>500 | Thr | Val | |
| CCC | GCA | AAC | TGG | GAT | CCC | TAC | ACC | CTG | GAA | GAT | GAC | AAC | TAC | CTG | GAA | 1584 |
| Pro | Ala | Asn<br>505 | Trp | Asp | Pro | Tyr | Thr<br>510 | Leu | Glu | Asp | Asp | Asn | Tyr<br>515 | Leu | Glu | |
| ATC | AAC | AAG | CAG | ATG | GAC | AGC | AAC | TCT | ATG | AAG | CTG | CAT | CTG | AGG | ACC | 1632 |
| Ile | Asn<br>520 | Lys | Gln | Met | Asp | Ser<br>525 | Asn | Ser | Met | Lys | Leu<br>530 | His | Leu | Arg | Thr | |
| AAC | TAC | CTG | CAG | TTC | TGG | ACC | CAG | ACC | TAC | CAG | GCC | CTG | CCC | ACG | GTG | 1680 |
| Asn | Tyr | Leu | Gln | Phe | Trp | Thr | Gln | Thr | Tyr | Gln | Ala | Leu | Pro | Thr | Val | |
| 535 | | | | 540 | | | | | 545 | | | | | | 550 | |
| ACC | AGC | GCG | GGG | GCC | AGC | CTG | CTG | CCC | CCC | GAG | GAC | AAC | TCT | CAG | GCC | 1728 |
| Thr | Ser | Ala | Gly<br>555 | Ala | Ser | Leu | Leu | Pro | Pro<br>560 | Glu | Asp | Asn | Ser | Gln<br>565 | Ala | |
| AGC | CCC | GTG | CCC | CCA | GCG | GAC | AAC | TCC | GGG | GCT | CCC | ACC | GAA | CCC | TCT | 1776 |
| Ser | Pro | Val<br>570 | Pro | Pro | Ala | Asp | Asn | Ser<br>575 | Gly | Ala | Pro | Thr | Glu<br>580 | Pro | Ser | |
| GCG | GGT | GAC | TCT | GAG | GTG | GCT | CAG | ATG | CCT | GTC | GTC | ATT | GGT | TTC | | 1821 |
| Ala | Gly | Asp | Ser<br>585 | Glu | Val | Ala | Gln<br>590 | Met | Pro | Val | Val | Ile<br>595 | Gly | Phe | | |

TAATGTCCTT GGCCTCCAGG GGCCACAGGA GACCCCAGGG CCCACTTCCC     1871

TTCCCAAGTG CCTCCTGAAT AAAGCCTCAA CCATCTC     1908

( 2 ) INFORMATION FOR SEQ ID NO:3:

( i ) SEQUENCE CHARACTERISTICS:
        ( A ) LENGTH: 605 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Arg | Gln | Thr | Leu<br>-5 | Thr | Met | Gly | Arg | Leu<br>1 | Gly | Ala | Ser | Arg<br>5 | Leu | Gly | Pro |
| Ser | Pro<br>10 | Gly | Cys | Leu | Ala | Val<br>15 | Ala | Ser | Ala | Ala | Lys<br>20 | Leu | Gly | Ser | Val |
| Tyr<br>25 | Thr | Glu | Gly | Gly<br>30 | Phe | Val | Glu | Gly | Val<br>35 | Asn | Lys | Lys | Leu | Ser | Leu<br>40 |
| Phe | Gly | Asp | Ser | Val<br>45 | Asp | Ile | Phe | Lys | Gly<br>50 | Ile | Pro | Phe | Ala | Ala<br>55 | Ala |
| Pro | Lys | Ala | Leu<br>60 | Glu | Lys | Pro | Glu | Arg<br>65 | His | Pro | Gly | Trp | Gln<br>70 | Gly | Thr |
| Leu | Lys | Ala<br>75 | Lys | Ser | Phe | Lys | Lys<br>80 | Arg | Cys | Leu | Gln | Ala<br>85 | Thr | Leu | Thr |
| Gln | Asp<br>90 | Ser | Thr | Tyr | Gly | Asn<br>95 | Glu | Asp | Cys | Leu | Tyr<br>100 | Leu | Asn | Ile | Trp |
| Val<br>105 | Pro | Gln | Gly | Arg | Lys<br>110 | Glu | Val | Ser | His | Asp<br>115 | Leu | Pro | Val | Met | Ile<br>120 |
| Trp | Ile | Tyr | Gly | Gly<br>125 | Ala | Phe | Leu | Met | Gly<br>130 | Ser | Gly | Gln | Gly | Ala<br>135 | Asn |
| Phe | Leu | Lys<br>140 | Asn | Tyr | Leu | Tyr | Asp<br>145 | Gly | Glu | Glu | Ile | Ala<br>150 | Thr | Arg | Gly |

```
Asn  Val  Ile  Val  Val  Thr  Phe  Asn  Tyr  Arg  Val  Gly  Pro  Leu  Gly  Phe
          155                 160                 165

Leu  Ser  Thr  Gly  Asp  Ser  Asn  Leu  Pro  Gly  Asn  Tyr  Gly  Leu  Trp  Asp
     170                 175                 180

Gln  His  Met  Ala  Ile  Ala  Trp  Val  Lys  Arg  Asn  Ile  Glu  Ala  Phe  Gly
185                      190                 195

Gly  Asp  Pro  Asp  Asn  Ile  Thr  Leu  Phe  Gly  Glu  Ser  Ala  Gly  Gly  Ala
200                 205                      210                      215

Ser  Val  Ser  Leu  Gln  Thr  Leu  Ser  Pro  Tyr  Asn  Lys  Gly  Leu  Ile  Lys
               220                 225                      230

Arg  Ala  Ile  Ser  Gln  Ser  Gly  Val  Gly  Leu  Cys  Pro  Trp  Ala  Ile  Gln
          235                 240                 245

Gln  Asp  Pro  Leu  Phe  Trp  Ala  Lys  Arg  Ile  Ala  Glu  Lys  Val  Gly  Cys
250                      255                      260

Pro  Val  Asp  Asp  Thr  Ser  Lys  Met  Ala  Gly  Cys  Leu  Lys  Ile  Thr  Asp
265                      270                 275                      280

Pro  Arg  Ala  Leu  Thr  Leu  Ala  Tyr  Lys  Leu  Pro  Leu  Gly  Ser  Thr  Glu
               285                 290                      295

Tyr  Pro  Lys  Leu  His  Tyr  Leu  Ser  Phe  Val  Pro  Val  Ile  Asp  Gly  Asp
               300                 305                      310

Phe  Ile  Pro  Asp  Asp  Pro  Val  Asn  Leu  Tyr  Ala  Asn  Ala  Ala  Asp  Val
          315                 320                      325

Asp  Tyr  Ile  Ala  Gly  Thr  Asn  Asp  Met  Asp  Gly  His  Leu  Phe  Val  Gly
     330                      335                 340

Met  Asp  Val  Pro  Ala  Ile  Asn  Ser  Asn  Lys  Gln  Asp  Val  Thr  Glu  Glu
345                      350                 355                      360

Asp  Phe  Tyr  Lys  Leu  Val  Ser  Gly  Leu  Thr  Val  Thr  Lys  Gly  Leu  Arg
               365                 370                      375

Gly  Ala  Asn  Ala  Thr  Tyr  Glu  Val  Tyr  Thr  Glu  Pro  Trp  Ala  Gln  Asp
               380                 385                      390

Ser  Ser  Gln  Glu  Thr  Arg  Lys  Lys  Thr  Met  Val  Asp  Leu  Glu  Thr  Asp
          395                 400                      405

Ile  Leu  Phe  Leu  Ile  Pro  Thr  Lys  Ile  Ala  Val  Ala  Gln  His  Lys  Ser
     410                 415                      420

His  Ala  Lys  Ser  Ala  Asn  Thr  Tyr  Thr  Tyr  Cys  Phe  Ser  Gln  Pro  Ser
425                      430                 435                      440

Arg  Met  Pro  Ile  Tyr  Pro  Lys  Trp  Met  Gly  Ala  Asp  His  Ala  Asp  Asp
                    445                 450                      455

Leu  Gln  Tyr  Val  Phe  Gly  Lys  Pro  Phe  Ala  Thr  Pro  Leu  Gly  Tyr  Arg
               460                 465                      470

Ala  Gln  Asp  Arg  Thr  Val  Ser  Lys  Ala  Met  Ile  Ala  Tyr  Trp  Thr  Asn
          475                 480                      485

Phe  Ala  Arg  Thr  Gly  Asp  Pro  Asn  Thr  Gly  His  Ser  Thr  Val  Pro  Ala
     490                 495                 500

Asn  Trp  Asp  Pro  Tyr  Thr  Leu  Glu  Asp  Asp  Asn  Tyr  Leu  Glu  Ile  Asn
505                      510                 515                      520

Lys  Gln  Met  Asp  Ser  Asn  Ser  Met  Lys  Leu  His  Leu  Arg  Thr  Asn  Tyr
               525                 530                      535

Leu  Gln  Phe  Trp  Thr  Gln  Thr  Tyr  Gln  Ala  Leu  Pro  Thr  Val  Thr  Ser
               540                 545                      550

Ala  Gly  Ala  Ser  Leu  Leu  Pro  Pro  Glu  Asp  Asn  Ser  Gln  Ala  Ser  Pro
          555                 560                      565

Val  Pro  Pro  Ala  Asp  Asn  Ser  Gly  Ala  Pro  Thr  Glu  Pro  Ser  Ala  Gly
     570                 575                      580
```

Asp Ser Glu Val Ala Gln Met Pro Val Val Ile Gly Phe
585                 590                 595

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Asp Gly His Leu Phe Ala Thr Val Asp Val Pro Ala Ile Asp
1               5                   10                  15

Lys Ala Lys Gln Asp Val
            20

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Lys Lys Arg Cys Leu Gln
1               5

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Pro Ala Ile Asn Lys Gly Asn Lys Lys Val
1               5                   10

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Pro Ala Ile Asp Lys Ala Lys Gln Asp Val
1               5                   10

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:8:

```
Pro Ala Ile Asn Ser Asn Lys Gln Asp Val
 1               5                   10
```

( 2 ) INFORMATION FOR SEQ ID NO:9:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

CCTGCCATCA ACAAGGGCAA CAAGAAAGTC    30

( 2 ) INFORMATION FOR SEQ ID NO:10:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: misc_feature
      ( B ) LOCATION: 1..30
      ( D ) OTHER INFORMATION: /note= "oligonucleotide probe
         mixture."

( x i ) SEQUENCE DESCRIPTION: SEQ ID NO:10:

NCCTYCCACA ARGCCGCCTT CGGYATACAS    30

( 2 ) INFORMATION FOR SEQ ID NO:11:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:11:

```
Lys Lys Arg Cys Leu Trp
 1               5
```